(12) United States Patent
David et al.

(10) Patent No.: US 9,310,264 B2
(45) Date of Patent: Apr. 12, 2016

(54) DEVICE, METHOD AND SYSTEM FOR ADD ON ATTACHMENT OF APPLIED FORCE STRAIN SENSOR ONTO EXERCISE EQUIPMENT

(71) Applicant: WATTEAM LTD, Yodfat (IL)

(72) Inventors: Eliyahu David, Doar Na Misgav (IL); Ofir Gal-On, Yodfat (IL)

(73) Assignee: WATTEAM LTD, Yodfat (IL)

( * ) Notice: Subject to any disclaimer, the term of this patent is extended or adjusted under 35 U.S.C. 154(b) by 0 days.

(21) Appl. No.: 13/969,659

(22) Filed: Aug. 19, 2013

(65) Prior Publication Data

US 2013/0333489 A1    Dec. 19, 2013

Related U.S. Application Data

(63) Continuation-in-part of application No. PCT/IL2012/000084, filed on Feb. 16, 2012.

(60) Provisional application No. 61/444,733, filed on Feb. 19, 2011.

(51) Int. Cl.
G01L 1/04 (2006.01)
G01L 1/22 (2006.01)
G01L 3/14 (2006.01)
(Continued)

(52) U.S. Cl.
CPC ............. *G01L 1/044* (2013.01); *A61B 5/221* (2013.01); *A61B 5/6895* (2013.01); *A63B 22/0605* (2013.01); *A63B 69/16* (2013.01); *B62M 3/00* (2013.01); *B62M 6/50* (2013.01); *G01L 1/2225* (2013.01); *G01L 3/1457* (2013.01); *G01L 5/225* (2013.01); *A61B 2562/0261* (2013.01); *A63B 2220/24* (2013.01); *A63B 2220/34* (2013.01); *A63B 2220/54* (2013.01);

(Continued)

(58) Field of Classification Search
CPC .......... B62M 23/02; B62M 3/08; G01N 3/00; G01L 1/22; G01L 1/04; A63B 24/00
USPC ....................................................... 73/862.641
See application file for complete search history.

(56) References Cited

U.S. PATENT DOCUMENTS

| 4,423,630 A | 1/1984 | Morrison |
| 5,031,455 A | 7/1991 | Cline |
| 5,257,540 A | 11/1993 | Bower et al. |
| 5,591,908 A | 1/1997 | Reid |

(Continued)

FOREIGN PATENT DOCUMENTS

WO    0220094 A1    3/2002

OTHER PUBLICATIONS

International Search Report dated Jul. 20, 2012, in corresponding International Application No. PCT/IL2012/000084.

*Primary Examiner* — Lisa Caputo
*Assistant Examiner* — Octavia Hollington

(57) ABSTRACT

A device, method, and system that allows the easy add on attachment of an applied-power sensor, assuring precise measurements over time, even in vibrating environments such as exercise environments. The device possesses structural qualities such that tightening the wrapping latch around a measured object/part presses a loaded spring between the object/part and the sensor, achieving and maintaining sufficient and constant contact, thus allowing continuously precise measuring. The device also includes a transmitter to transmit the measured data to an external data processing device and may include a processor to process the data before transmitting.

16 Claims, 7 Drawing Sheets

(51) Int. Cl.
*A63B 69/16* (2006.01)
*A63B 22/06* (2006.01)
*B62M 3/00* (2006.01)
*G01L 5/22* (2006.01)
*B62M 6/50* (2010.01)
*A61B 5/00* (2006.01)
*A61B 5/22* (2006.01)

(52) U.S. Cl.
CPC ...... *A63B 2220/72* (2013.01); *A63B 2220/833* (2013.01); *A63B 2225/50* (2013.01); *B62J 2300/002* (2013.01)

(56) References Cited

U.S. PATENT DOCUMENTS

| | | | |
|---|---|---|---|
| 5,758,735 | A | 6/1998 | MacCready, Jr. et al. |
| 6,418,797 | B1 | 7/2002 | Ambrosina et al. |
| 6,886,416 | B2 * | 5/2005 | Tsay et al. ............... 73/862.321 |
| 7,257,468 | B1 | 8/2007 | Costa et al. |
| 7,599,806 | B2 | 10/2009 | Hauschildt |
| 7,775,128 | B2 | 8/2010 | Roessingh et al. |
| 7,806,006 | B2 | 10/2010 | Phillips et al. |
| 8,011,242 | B2 * | 9/2011 | O'Neill et al. ............. 73/379.01 |
| 2005/0178210 | A1 | 8/2005 | Lanham |
| 2010/0018307 | A1 | 1/2010 | Furuta et al. |

* cited by examiner

DEVICE, METHOD AND SYSTEM FOR ADD ON ATTACHMENT OF APPLIED FORCE STRAIN SENSOR ONTO EXERCISE EQUIPMENT

FIELD OF THE INVENTION

The present invention relates to the fields of athletic exercise and recreational devices and equipment, and to a device, method and system for attaching, measuring and displaying precise forces applied by the user of such devices. More specifically, the present invention allows the add-on attachment of force-measuring-sensors to moving parts in exercise apparatuses, with no recourse to the dismantling of any mechanisms or parts, in a way which maintains continuously precise measurements.

BACKGROUND OF THE INVENTION

It is necessary in the field of athletic exercise to provide people (such as bicycle riders) who are interested in their level of performance, in particular their power output, with add-on applied-force sensor device which is easy to attach and is able to produce and transmit precise measurements even in a vibrating environment. Applications include for example, measuring and displaying the driving torque applied to the crank arm in stationary or usual bicycle. To that end, the prior art, such as (U.S. Pat. Nos. 7,775,128B2; 7,806,006B2; 7,599,806B2; 7,257,468B1; 6,418,797B1; 5,758,735; 5,591,908; 5,257,540; 5,031,455; 4,423,630), teaches a method and device of applied force sensing device for use while cycling.

Although various devices are known, the known devices of the prior art fail to provide a solution for an applied-force sensing-device which can be added on to exercise apparatuses such as bicycle, without dismantling and/or replacing certain mechanisms, for example the bicycle gear system, pedals or the crank arm, or crank spider in a manner that allows precise measuring.

Exercise environments often introduce reaction forces such as vibration. In these environments, sensors must be installed and anchored to firmly grip the measured object/part, for achieving precise measurements over time. For bicycle raiders in particular, to achieve and maintain precise measuring, installation of applied-force sensing-devices often requires the dismantling of mechanisms and replacing the original parts with specialized parts. These parts are often very expensive and usually require professional person expertise to install and maintain.

An applied force measuring arrangement is already known as Strain Gage, used to measure the strain forces applied to a surface or object. For example see Transducer-Class® Strain Gages, part number: S1425 or S120P, made by Full Bridge Patterns, Vishay Micro-Measurements. Strain force measuring requires the anchoring of the sensor to the measured surface for maximizing the direct transferring of forces. Furthermore, continuous pressure is also required, to maintain constant and firm contact between the strain sensor and the measured surface or object.

To date, there are no satisfactory add-on devices and methods for applied-force sensing-devices, which offer easy add-on installation to different types of exercise devices, do not require any action of dismantling any mechanisms and/or replacing any original parts, and maintain precise measurements in an exercising environment. Thus, there remains a need in the art for an improved add-on device and method.

In addition, there is an increasing commercial demand for personal training applications, such as smart phones application designed to work with different athletic exercise devices (for example see the Edge 800® and Edge 500®, made by GARMIN; Node 1 and Node 2, made by Bontrager Node computers). There is a need to provide a system and method for easy add-on attachment of applied-force measuring device, able to continuously measure precise forces and transmit them to an external device for processing and display, using for example, wireless protocols.

SUMMARY OF THE INVENTION

It is hence one object of the invention to disclose a device for measuring a force applied to a bicyclical pedal by a rider. The aforesaid device is attachable to a pedal crank. The device comprises (a) attaching means quickly embracing and detaching from said crank arm; (b) a spring-loaded leaf; (c) at least one strain sensor adapted to measure a strain of said spring-loaded leaf and a control unit.

Another object of the invention is to disclose said spring-loaded leaf attached along a direction of bending deformation of said crank arm.

A further object of the invention is to disclose the spring-loaded leaf attached along a direction of twisting deformation of said crank arm and pedal.

A further object of the invention is to disclose spring-loaded leaf which is glued to the crank.

A further object of the invention is to disclose the control unit further comprising at least one component selected from the group consisting of an amplifier, an analog-to-digital converter, a microprocessor, a wireless communication interface, display means and a data transponder.

A further object of the invention is to disclose at least one component connected to said control unit which is selected from the group consisting of a sensor of crank angular displacement, a temperature sensor and a pedal cadence sensor.

A further object of the invention is to disclose the control unit preprogrammed for auto-calibration.

A further object of the invention is to disclose a method of measuring a force applied to a bicyclical pedal by a rider. The aforesaid method comprises the steps of: (a) providing a device for measuring a force applied to a bicyclical pedal by a rider; said device is attachable to a pedal crank arm; said device comprises (i) attaching means quickly embracing and detaching from said crank arm; (ii) a spring-loaded leaf; (iii) at least one strain sensor adapted to measure a strain of said spring-loaded leaf (iv) a control unit; (b) attaching said device to said crank arm; (c) applying a turning torque to said crank arm by said rider; (d) elastically deforming said crank arm by said turning torque; (e) measuring said deformation by means of said strain sensor.

A further object of the invention is to disclose the step of measuring said deformation comprising measuring bending deformation of said crank.

A further object of the invention is to disclose the step of measuring said deformation comprising measuring twisting deformation of said crank arm and pedal.

BRIEF DESCRIPTION OF THE DRAWINGS

The subject matter regarded as the invention is particularly pointed out and distinctly claimed in the following portion of the description. The invention, however, both as to organization and method of operation, together with objects, features, and advantages thereof, may best be understood by reference to the following description when read with the accompanying drawings in which:

DESCRIPTION OF THE INVENTION

Figure 1A:
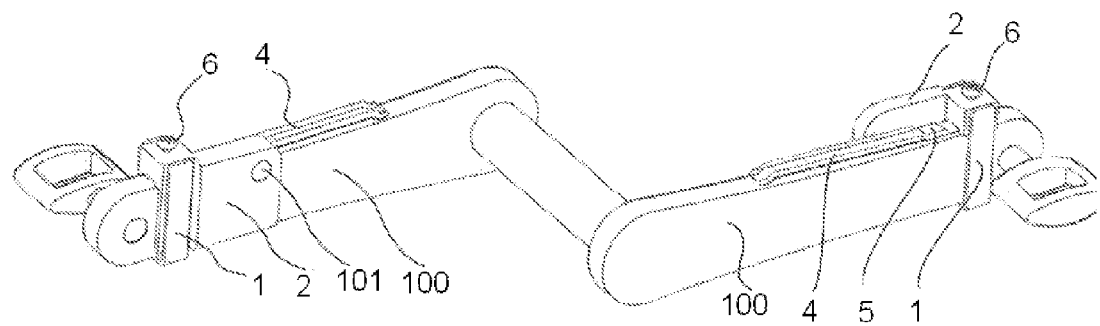
FIGS. 1a and 1b illustrate the device, installed on a bicycle crank arms.

In the following description, specific details are set forth in order to provide a thorough understanding of the invention. However, it will be understood by those skilled in the art that the present invention may be practiced without these specific details. In other instances, well-known methods, procedures and components have not been described in detail so as not to obscure the present invention.

The term "sensor" hereinafter refers to a pre-stressed leaf operatively connected to a strain gage. The aforesaid strain gage is configured for generation of an electric signal corresponding to a deformation of the pre-stressed leaf.

It should be emphasized that the claimed device of the present invention is designed for attaching to standard bicyclical articles and no improvement or modification of the bicyclical articles is needed.

According to some embodiments of the present invention, there is a provided an applied-force sensing device, method and system for people who take interest in their performance during athletic activity, which device and/or method and/or system may be described in view of FIGS. 1-7.

A primary function of the invention is to provide the means to improve the ease of installation of applied-force sensing-devices, while assuring continuous precise measurements over time in an exercise environment, by allowing users to tightly attach the device to a measured object in a manner which creates constant pressure, ensuring the consecutiveness of contact required for sensitive and precise measuring.

According to some embodiments of the present invention the device may be shaped as a case hosting electronic components (2) made of resilient material such as Metal or plastic shell.

According to some embodiments of the present invention, the device may include at least one applied-force sensor such as a strain-gage (5), cased in the shell (2) and provided with a spring loaded leaf (4) for measuring the force applied to an exercise object.

According to some embodiments of the present invention, a spring-loaded 'leaf' (4) is firmly connected to a measured object. Accordingly, the spring-loaded 'leaf' (4) may indicate the strain force applied to the object/part/crank arm/pedal (100), to be measured by the strain-sensor (5).

According to some embodiments of the present invention, the spring-loaded leaf 110 provided with a strain gage 120 (see an enlarged view in FIG. 4b) is glued to the pedal crank 100. The leaves 110 with strain gages 120 can be attached in any locations indicated in FIG. 4c. Each sensor should be calibrated according to its location on the pedal crank. Control unit (not shown) can disposed in any convenient location.

According to some embodiments of the present invention, the means (1) for attaching the device to the object/part, may allow the attachment of the device to the object/part/crank arm, by tightening the latch (1) which is wrapped around the object/part (100), using screw arrangement (6). Accordingly, tightening the wrapping latch around the object/part (100), presses the spring-loaded 'leaf' (4) against the object/part (100), applying constant force downward, thus maintaining constant tightened contact between the sensor (5) and the measured object/part (100).

Figure 1B:
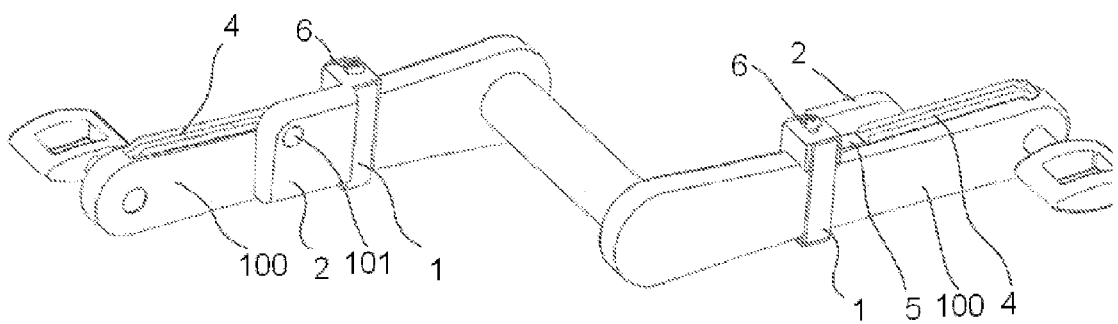
Figure 2:
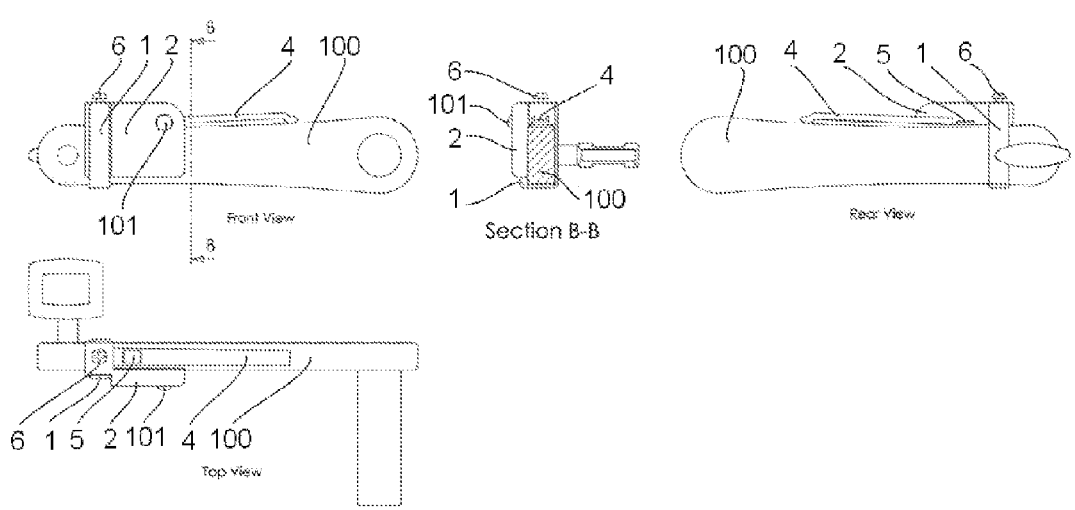
FIG. 2 presents front, rear, top and cross-sectional views of the device installed on the inner side of a bicycle crank arm.
Figure 3A:
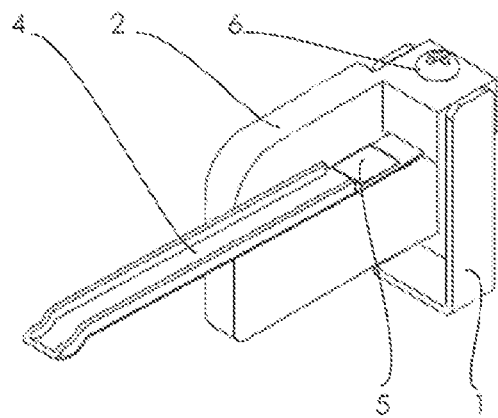
FIGS. 3a and 3b illustrate a perspective view of the device installable onto a bicycle crank arm.
Figure 3B:
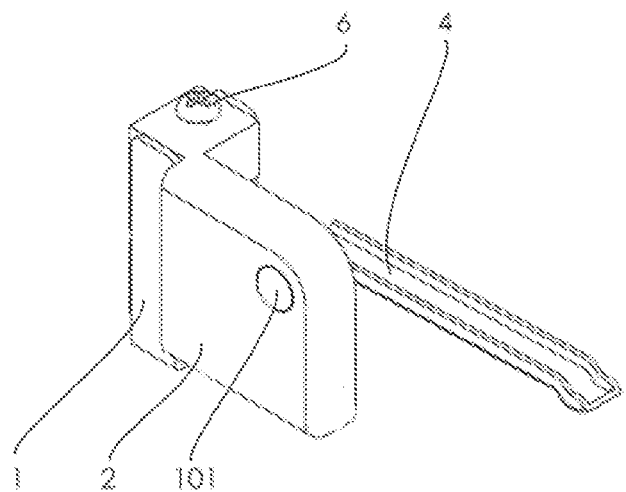
Figure 4A:
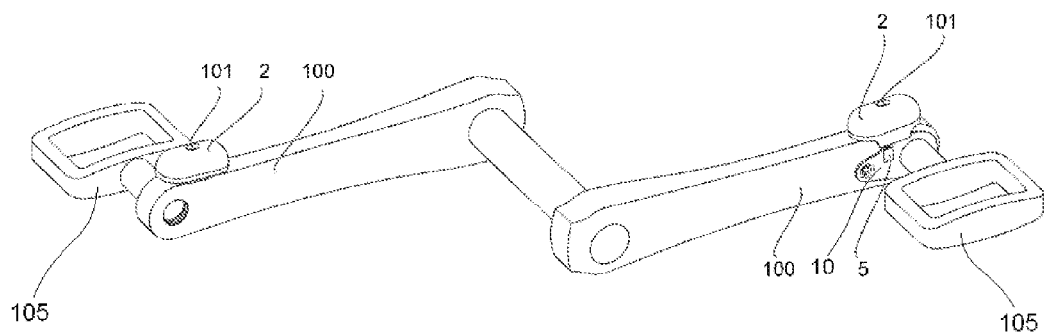
FIG. 4a illustrates the device, installed on a bicycle crank arm attached by a pedal.
Figure 4B:
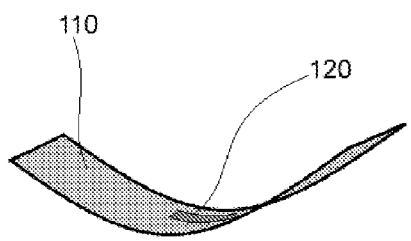
FIG. 4b illustrates a spring-loaded leaf provided with a strain gage.
Figure 4C:
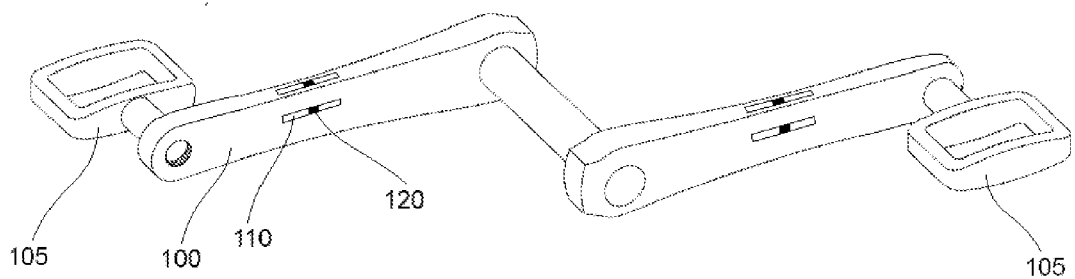
FIG. 4c illustrates the spring-loaded leaf glued to a bicycle crank arm.
Figure 5A:
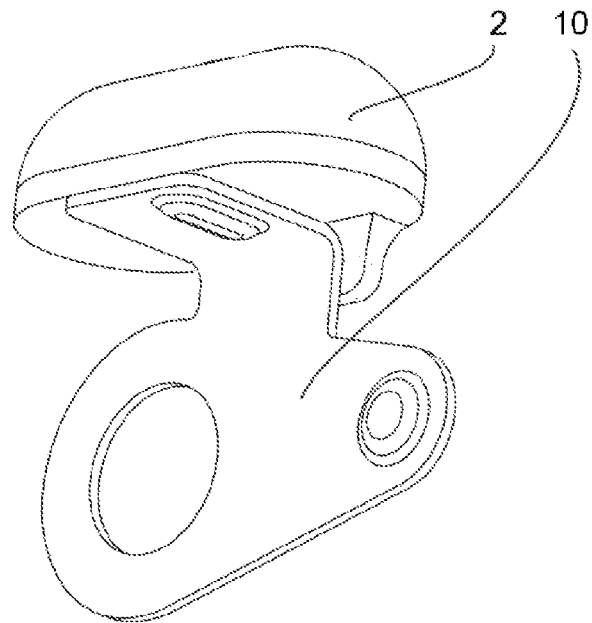
FIGS. 5a and 5b present views of the device installable onto a bicycle crank attached by a pedal.
Figure 5B:
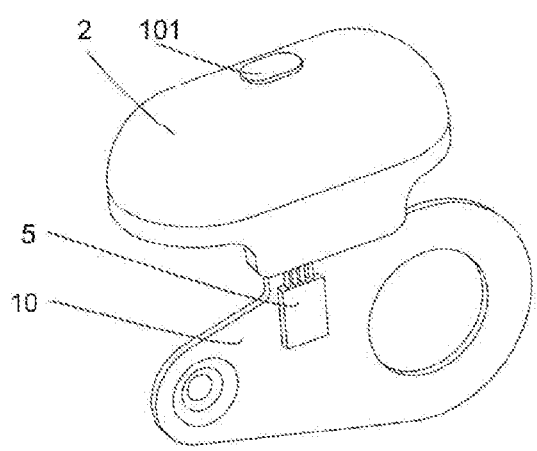

According to some embodiments of the present invention, the attachment of the device may be done on different positions on the exercise device/object, for example, on either side of the crank arm of a bicycle (see FIG. 1A and FIG. 1B). The above mentioned embodiment is configured for measuring elastic bending deformation of the crank arm.

Figure 6:
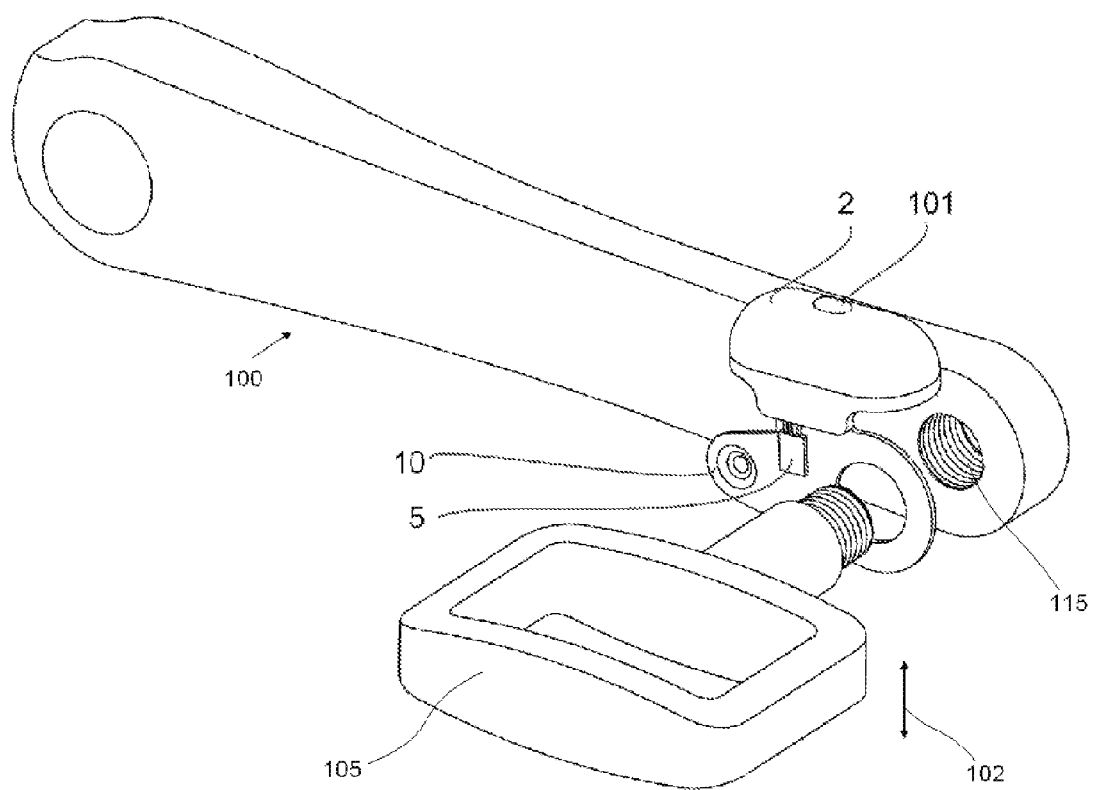
FIG. 6 is an exploded view of the device, installed on a bicycle pedal.
Figure 7:
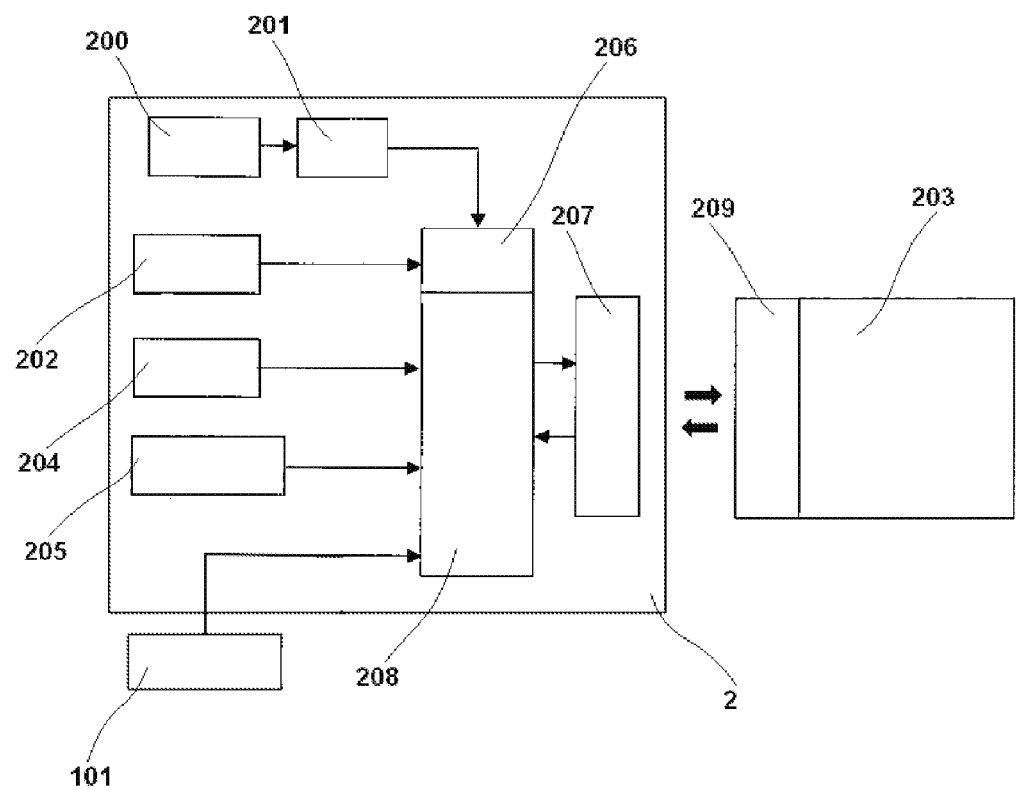
FIG. 7 is a schematic diagram of the main electronic components in the device, according to some embodiments of the present invention.

In accordance with another embodiment of the present, the device is configured for measuring elastic twisting deformation of the crank arm and pedal as shown in FIG. 6. A twisting force is applied to a pedal 105 by a rider (not shown) and is transferred to the crank arm 100. The aforesaid force is applied along an arrow 102. The rider can press down onto the pedal 105 and pull it up when the rider's foot is fixedly attached to the pedal 105. The pedal 105 is connected to a threaded opening 115 in the crank arm 100. The spring-loaded member 10 is firmly connected to the crank arm 100 by the pedal 105. The strain gage 5 provides a change in electric impedance corresponding to deformation of the member 10. The aforesaid deformation corresponds to deformation in the crank arm 100 and the pedal 105.

According to some embodiments of the present invention, the device may include all or some of the following components (see FIG. 7): strain sensors (200); electronic sensor amplifier (201); pedal cadence sensor (202); temperature sensor (204); crank arm angular displacement sensor (205); A/D converter (206); a transmitting device (207); a microprocessor (208) and wireless communication means 209.

According to some embodiments of the present invention, the users may operate the system by pressing the calibration button arrangement (101) to calibrate the applied force measurement sensor before each exercise activity.

According to some embodiments of the present invention, the calibration process may be done automatically by calculation processes in the microprocessor (208), or by calculation processes in the external wireless device (203).

According to some embodiments of the present invention, the device may include a transmitting device (207) for transmitting the measured data to an external wireless device (203). Data may be transmitted using wireless protocols for example RF, Bluetooth.

In accordance with these and other objects, this invention provides a means structured to allow easy add-on attachment of the sensing device to the measured exercise object/part, to provide constant tightened contact between the sensing device and the measured object even under constant vibrations and to directly process and transmit the measured data to an external device, thus improving the integration and ease of use of exercise enhancing applications.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

The invention claimed is:

1. A device for measuring a force applied to a bicyclic pedal by a rider; said device attachable to a standard bicyclic crank carrying said pedal secured thereto; said device comprising:
   a. attaching means adapted for quickly embracing and detaching from said crank;
   b. a spring-loaded leaf attached to said crank; said spring-loaded leaf configured for measuring deformation of said crank;
   c. at least one strain gauge adapted to measure a strain of said spring-loaded leaf; said strain gauge configured for indicating crank deformation; and
   d. a control unit.

2. The device according to claim 1, wherein said spring-loaded leaf is attached along a direction of bending deformation of said crank arm.

3. The device according to claim 1, wherein said spring-loaded leaf is attached along a direction of twisting deformation of said crank arm and a pedal.

4. The device according to claim 1, wherein said spring-loaded leaf is glued to said crank.

5. The device according to claim 1, wherein said control unit further comprises at least one component selected from the group consisting of an amplifier, an analog-to-digital converter, a microprocessor, a wireless communication interface, display means and a data transponder.

6. The device according to claim 5, wherein at least one component connected to said control unit is selected from the group consisting of a sensor of crank angular displacement, a temperature sensor and a pedal cadence sensor.

7. The device according to claim 1, wherein said control unit is preprogrammed for auto-calibration.

8. The device according to claim 1, further comprising a case, wherein the at least one strain gauge is disposed within the case and directly connected to the spring-loaded leaf.

9. The device according claim 1, further comprising a calibration button arrangement adapted to calibrate the strain-gauge.

10. A method of measuring a force applied to a bicyclical pedal by a rider; said method comprising the steps of:
   a. providing a device for measuring a force applied to a bicyclic pedal by a rider; said device attachable to a standard bicyclic crank carrying said pedal secured thereto; said device comprising
      i. attaching means adapted for quickly embracing and detaching from said crank;
      ii. a spring-loaded leaf attached to said crank; said spring-loaded leaf configured for measuring deformation of said crank;
      iii. at least one strain gauge adapted to measure a strain of said spring-loaded leaf; said strain gauge configured for indicating crank deformation;
      iv. a control unit;
   b. attaching said device to said crank;
   c. applying a turning torque to said crank by said rider;
   d. elastically deforming said crank by said turning torque; and
   e. measuring deformation by means of said strain sensor.

11. The method according to claim 10, wherein said step of measuring said deformation comprises measuring bending deformation of said crank arm.

12. The method according to claim 10, wherein said step of measuring deformation comprises measuring twisting deformation of said crank arm and pedal.

13. The method according to claim 10, wherein said step of attaching said device to said crank comprising gluing said device to said crank.

14. The method according to claim 10, wherein said device is provided with control unit further comprising at least one component selected from the group consisting of an amplifier, an analog-to-digital converter, a microprocessor, a wireless communication interface, display means and a data transponder.

15. The method according to claim 14, wherein at least one component connected to said control unit is selected from the group consisting of a sensor of crank angular displacement, a temperature sensor and a pedal cadence sensor.

16. The method according to claim 10, wherein said control unit is preprogrammed for auto-calibration.

* * * * *